US012672964B2

(12) United States Patent
Ghaednia et al.

(10) Patent No.: US 12,672,964 B2
(45) Date of Patent: Jul. 7, 2026

(54) EXPANDABLE LAMINOPLASTY IMPLANT

(71) Applicant: THE GENERAL HOSPITAL CORPORATION, Boston, MA (US)

(72) Inventors: Hamid Ghaednia, Boston, MA (US); Kartik Mangudi Varadarajan, Boston, MA (US); Joseph H. Schwab, Boston, MA (US); Soheil Ashkani Esfahani, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 131 days.

(21) Appl. No.: 18/556,379

(22) PCT Filed: Apr. 22, 2022

(86) PCT No.: PCT/US2022/025880

§ 371 (c)(1),
(2) Date: Oct. 20, 2023

(87) PCT Pub. No.: WO2022/226264

PCT Pub. Date: Oct. 27, 2022

(65) Prior Publication Data

US 2024/0358519 A1    Oct. 31, 2024

Related U.S. Application Data

(60) Provisional application No. 63/178,308, filed on Apr. 22, 2021.

(51) Int. Cl.
*A61F 2/44* (2006.01)
*A61F 2/30* (2006.01)

(52) U.S. Cl.
CPC .............. *A61F 2/441* (2013.01); *A61F 2/442* (2013.01); *A61F 2002/30471* (2013.01); *A61F 2002/30518* (2013.01); *A61F 2002/30528* (2013.01); *A61F 2002/4435* (2013.01)

(58) Field of Classification Search
CPC .. A61F 2/44; A61F 2/441; A61F 2/442; A61F 2/4405; A61F 2/46; A61F 2/4611; A61B 17/70; A61B 17/7071
See application file for complete search history.

(56) References Cited

U.S. PATENT DOCUMENTS

| | | | |
|---|---|---|---|
| 2021/0059655 A1* | 3/2021 | Boehm, Jr. | ........ A61B 17/7062 |
| 2022/0061901 A1* | 3/2022 | Linder | ............... A61B 17/8004 |

* cited by examiner

*Primary Examiner* — Christopher J Beccia
(74) *Attorney, Agent, or Firm* — Tarolli, Sundheim, Covell & Tummino LLP

(57) ABSTRACT

An implantable laminoplasty device is provided that can be used in minimally invasive surgery. The device includes a main housing with an inner housing slidably receivable by an outer housing. A gear is disposed in the main housing and engageable with a gear rack of the inner housing to adjust the length of the main housing. The gear defines an aperture configured to accept a tool to translate rotational movement into linear motion. A lock is slidably disposed in the main housing sized and configured to fix the length of the main housing when the desired length is achieved by slidable translation of the inner housing in the outer housing. The device also includes a laminar shelf portion and a lateral mass connection portion defining bone screws and both being hingedly connected to the main housing.

9 Claims, 11 Drawing Sheets

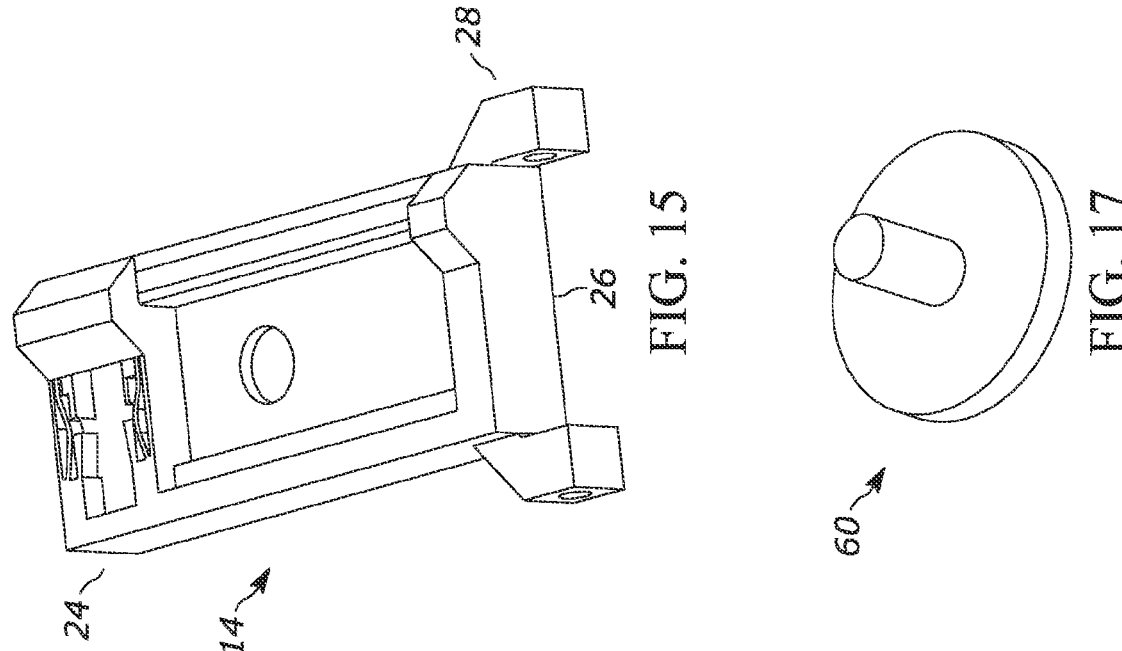
FIG. 15
FIG. 17
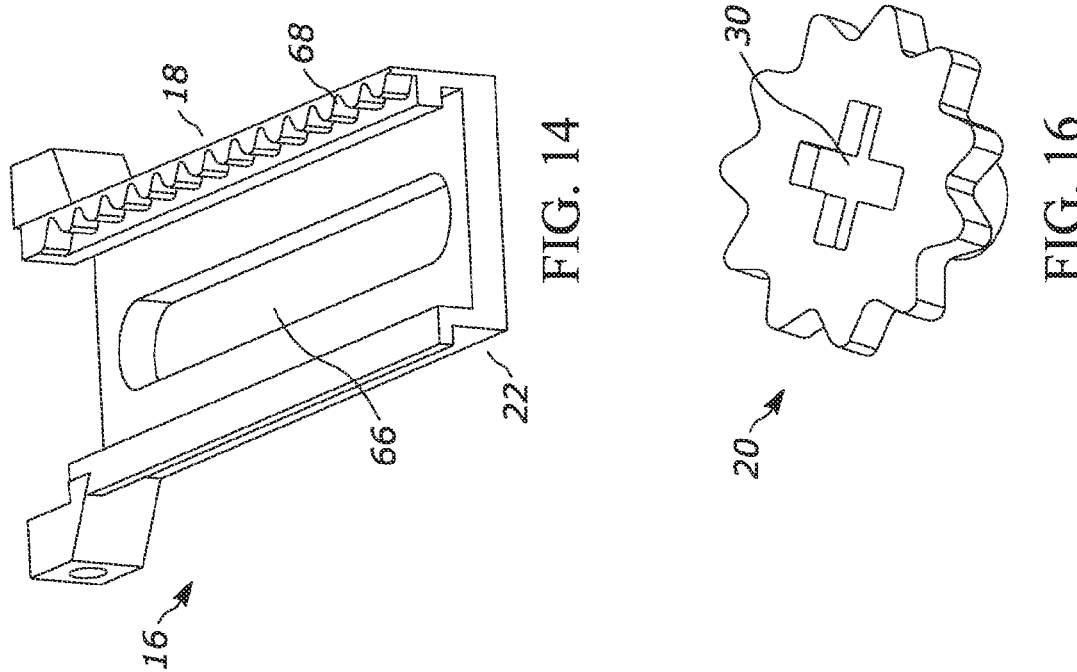
FIG. 14
FIG. 16

EXPANDABLE LAMINOPLASTY IMPLANT

RELATED APPLICATIONS

This application claims priority to U.S. Provisional Patent Application Ser. No. 63/178,308, filed Apr. 22, 2021. The entirety of the '308 application is hereby incorporated by reference.

TECHNICAL FIELD

The present disclosure relates to a medical device implant for minimally invasive spinal laminoplasty surgery.

BACKGROUND

Laminoplasty is a surgical procedure in which spinal cord compression is relieved through opening of the spinal cord. This is accomplished by creating hinges in the vertebral lamina overlying the spinal cord using implants to keep the lamina in a permanent open position. In laminoplasty, the lamina is lifted but not removed, thus avoiding the complications associated with laminectomy where the lamina bone (and associated muscle/tendon/tissue attachments) is removed permanently. Laminoplasty was developed to improve the postoperative complexities associated with laminectomy such as kyphosis, instability, axial neck pain, and range of motion. Minimally invasive surgery (MIS) techniques that preserve paraspinal muscle structures can reduce these long-term complications. However, implants and tools needed for these approaches are not readily available or not available at all. With the rapid uptake of robotic spinal surgeries, MIS procedures are expected to become significantly more common requiring the development of suitable implants.

Currently, several types of implants are used in cervical laminoplasty with the majority having a fixed length, and a few with adjustable length. Drawback of these implants include special tools needed for each implant, adjustable implants only allowing discrete expansion as opposed to continuous expansion, inability to control force exerted on the lamina thereby increasing risk of lamina fracture, screw loosening, and implant shapes that are not conducive for passing through MIS tubes.

Therefore, development of expandable implants that facilitate better bone fixation, can fit in MIS tubes used in minimally invasive techniques, and that use readily available surgical tools is needed.

SUMMARY

An implant is provided comprising a main housing comprising an outer housing and an inner housing slidably receivable by the outer housing. The inner housing includes a gear rack. A gear is disposed in the main housing and engageable with the gear rack of the inner housing to adjust the length of the main housing. The gear defining an aperture configured to accept a tool to translate rotational movement into linear motion. A lock is slidably disposed in the main housing sized and configured to fix the length of the main housing when the desired length is achieved by slidable translation of the inner housing in the outer housing. The implant includes a laminar shelf portion hingedly connected to a second end of the main housing, having a top portion, a side portion and a bottom portion sized and configured to be disposed against a lamina of a patient, the top portion defining bone screw holes extending therethrough. The implant also includes a lateral mass connection portion hingedly connected to a first end of the main housing, having a top side and a bottom side and a bone screw hole extending therethrough, the bottom side sized and configured to be disposed against a lateral mass of a vertebrae of the patient.

BRIEF DESCRIPTION OF THE DRAWINGS

FIG. 14 is a perspective view of an inner housing of a medical device according to an aspect of the present disclosure.

FIG. 15 is a perspective view of an outer housing of a medical device according to an aspect of the present disclosure.

FIG. 16 is a perspective view of a gear of a medical device according to an aspect of the present disclosure.

FIG. 17 is a perspective view of a gear holder of a medical device according to an aspect of the present disclosure.

DETAILED DESCRIPTION

Figures 1, 2:
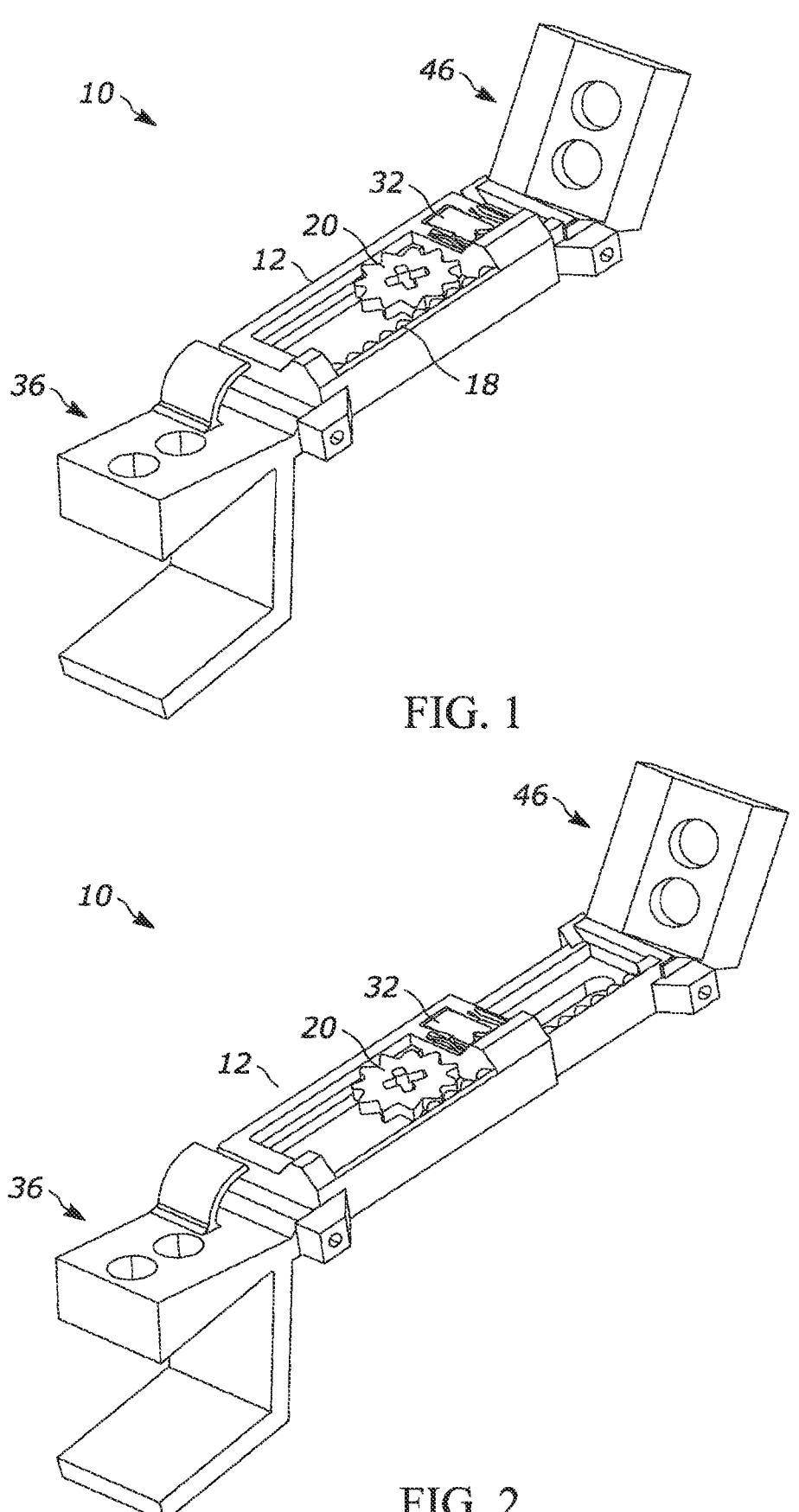
FIG. 1 is perspective view of a medical device in a non-extended configuration according to an aspect of the present disclosure.
FIG. 2 is a perspective view of the medical device of FIG. 1 in an extended configuration.

As used herein with respect to a described element, the terms "a," "an," and "the" include at least one or more of the described elements including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. A "patient" as described herein includes a mammal, such as a human being. The term "top," "bottom," "upper," "lower," "above," and "below," "left" and "right" refer to the position or orientation of the components as depicted in the drawings. The terms "first," "second," etc. are used to distinguish one element from another and not used in a quantitative sense unless indicated otherwise. The term "plurality" includes two or more of the described components. In addition, when an element is referred to as being "on," "attached" to, "connected" to, "coupled" with, "contacting," in "communication" with, "extending" from etc., another element, it can be directly on, attached to, connected to, coupled with, contacting, in communication with, or extending from the other element or intervening elements may also be present. In contrast, when an element is referred to as being, for example, "directly on," "directly attached" to, "directly connected" to, "directly coupled" with, "directly contacting," in "direct communication" with, or "directly extending" from another element, there are no intervening elements present. An element that is disposed "adjacent" to another element may have portions that overlap or underlie the adjacent element. By "integral" or "integrated" is meant that the described components are fabricated as one piece or multiple pieces affixed during manufacturing and the described components are otherwise not separable using a normal amount of force without damaging the integrity (i.e., tearing) of either of the components. A normal amount of force is the amount of force a user would use to remove a component meant to be separated from another component without damaging either component. All devices described herein are for medical purposes and are therefore sterile.

The present disclosure relates to medical implants that can be used in a laminoplasty procedure. The implants can be deployed through MIS tubes, use existing tools in an operating room, facilitate controlled force application to lamina with minimal bending on the spine, provide adjustable attachment angles, provide continuous expandability and allow implementation of open door and double door cervical laminoplasty with the same implant. With such adjustability and other features, an implant can address several of the challenges in laminoplasty. As the implant can be used in MIS, this can preserve muscle attachments and may reduce occurrence of post-operative complications such as axial neck pain, kyphosis, and C5 palsy.

Figure 3:
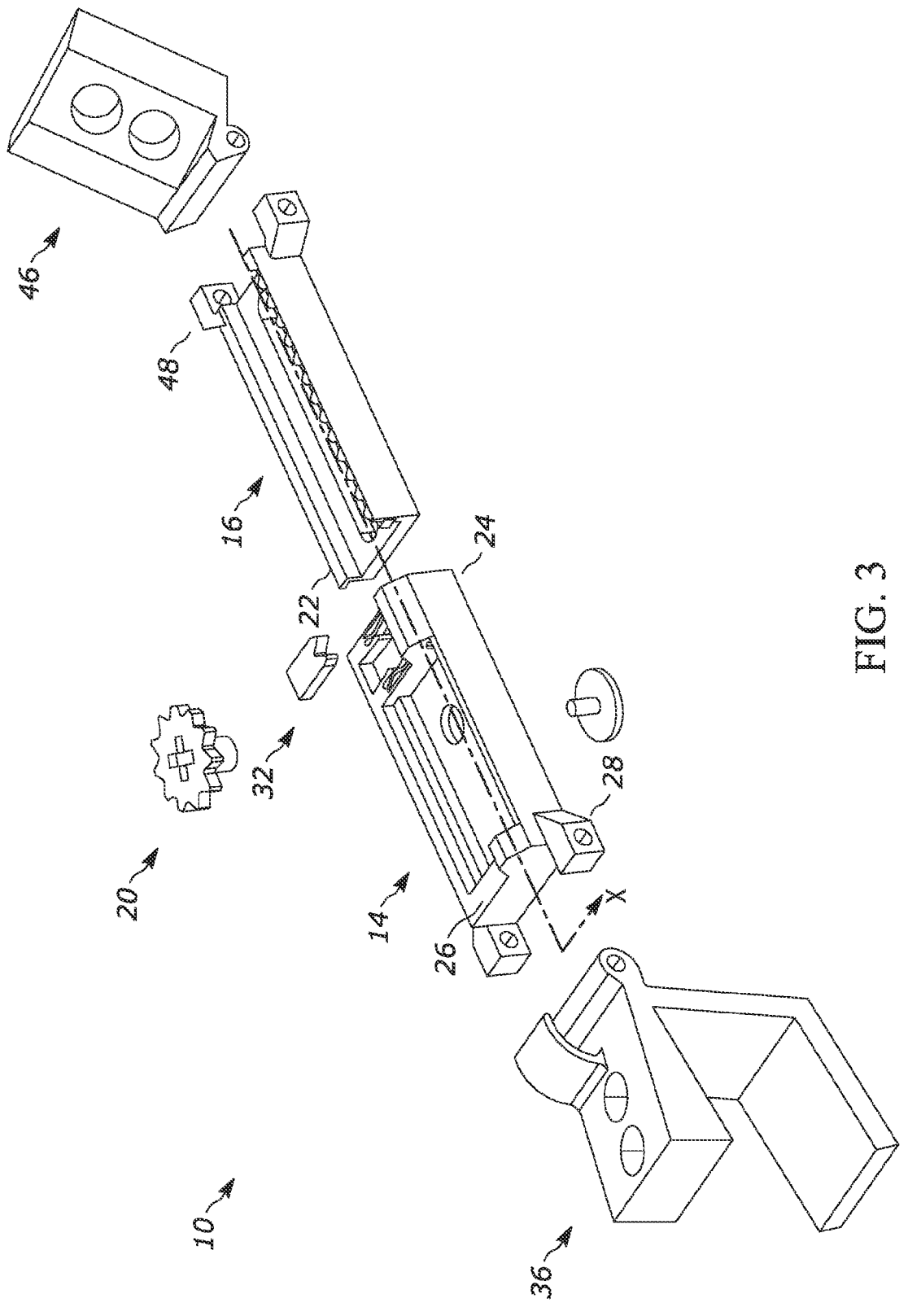
FIG. 3 is an exploded view of the medical device of FIG. 1.
Figures 18, 19, 20, 21:
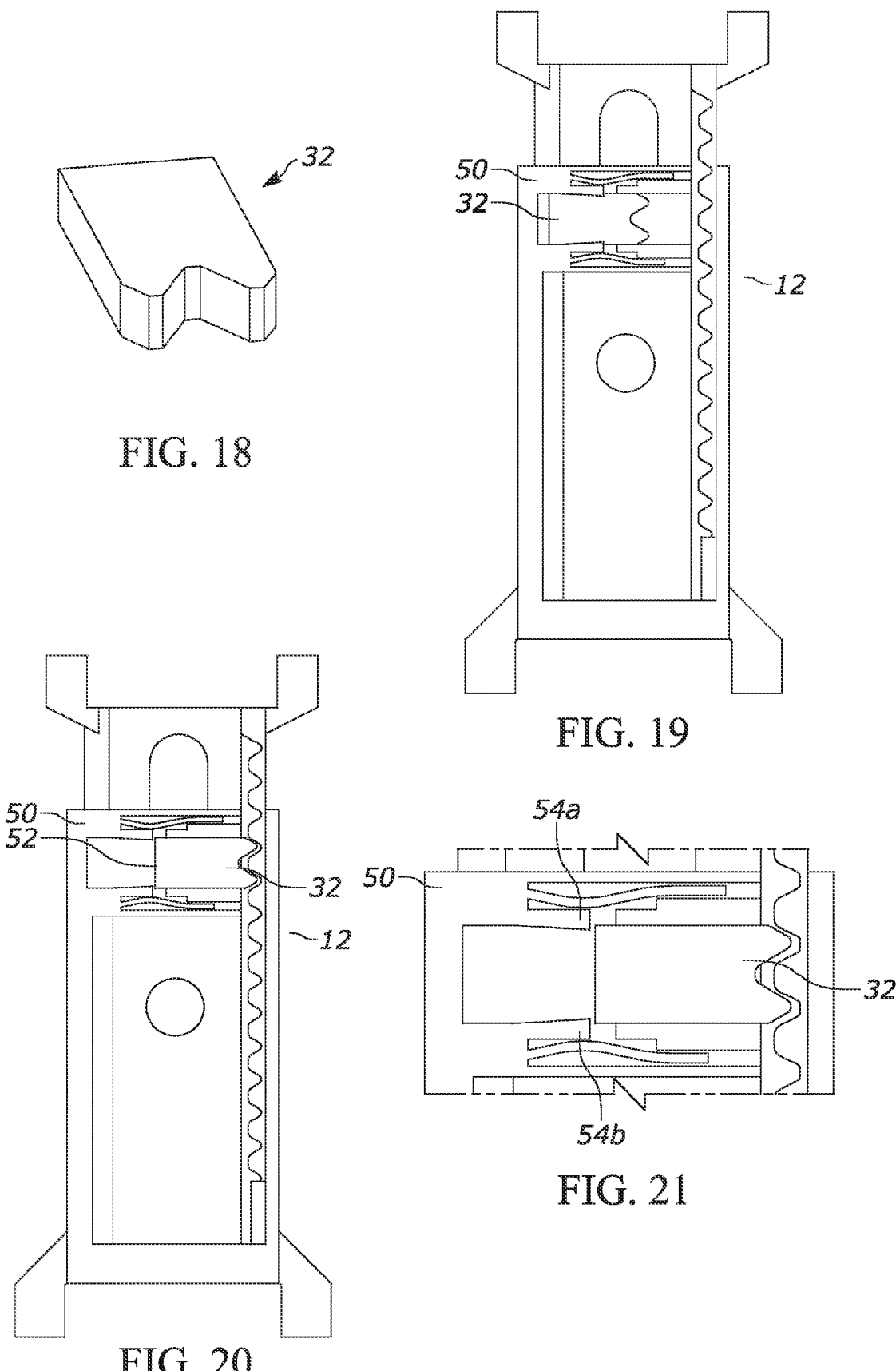
FIG. 18 is a perspective view of a lock of a medical device according to an aspect of the present disclosure.
FIG. 19 is a top view of an inner housing of a medical device according to an aspect of the present disclosure with a lock placed within a chamber of the inner housing according to an aspect of the present disclosure.
FIG. 20 is a top view of the inner housing of FIG. 18 with the lock in a locked position to constrain relative motion of the outer housing and the gear rack of the inner housing.
FIG. 21 is a close-up view of the chamber of the inner housing depicted in FIGS. 18 and 19.
Figure 23:
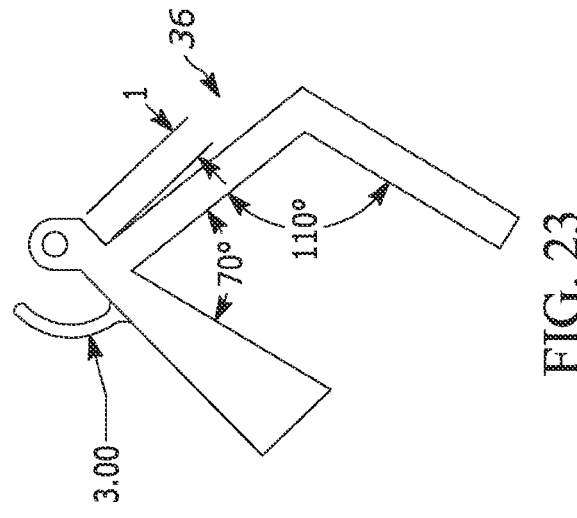
FIG. 23 is a side view of the laminar shelf portion of FIG. 22.

In an aspect and with reference to FIGS. 1-3, an implant 10 is provided that can comprise a main housing 12 having a longitudinal axis X and that can comprise outer housing 14 and inner housing 16, with inner housing 16 having a first end 22 received by a second end 24 of outer housing 14 and slidably extendable through outer housing 14 along longitudinal axis X until reaching an abutment wall 26 at second end 28 of outer housing 14 that prevents further longitudinal movement of inner housing 16 (inner housing 16 is shown in isolation in FIG. 14 and outer housing 24 is illustrated in isolation in FIG. 15). The outer housing effectively acts as the central part of the implant that connects all the components together. As shown in FIG. 14, inner housing 16 can include gear rack 18 which can slide through the outer housing. Gear 20 can be disposed in main housing 12 and can be engageable with gear rack 18 of inner housing 16 to adjust the length of main housing 12. In particular, the relative movement of the gear rack with respect to the outer housing is controlled by the rotation of the gear. Middle long hole 66 serves as a rail for the gear. Upon rotation, the gear interacts with gear rack teeth 68 to move in a linear direction. Referring to FIG. 16, gear 20 defines an aperture 30 configured to accept a tool, such as a screwdriver for example, to translate rotational movement into linear motion. The implant can include a gear holder 60 illustrated in FIGS. 6, 8 and 17 that can extend through the inner and outer housings and engage a socket of the gear to maintain the gear in place. Lock 32 (illustrated in FIG. 1-3 and FIGS. 18-21) can be slidably disposed in a chamber 50 of the main housing, such as outer housing 14, and can be sized and configured to fix the length of the main housing when the desired length is achieved by slidable translation of the inner housing in the outer housing. As such, the gear rack and the gear work in conjunction to control the length of the implant. With reference to FIGS. 19 and 20, lock 32 can be urged to the right, for example, until the lock (or a portion thereof) contacts springs(s) 54, for example, which can act as gear restraints to maintain the lock in place and prevent the lock from backing out of the chamber.

Figure 6:
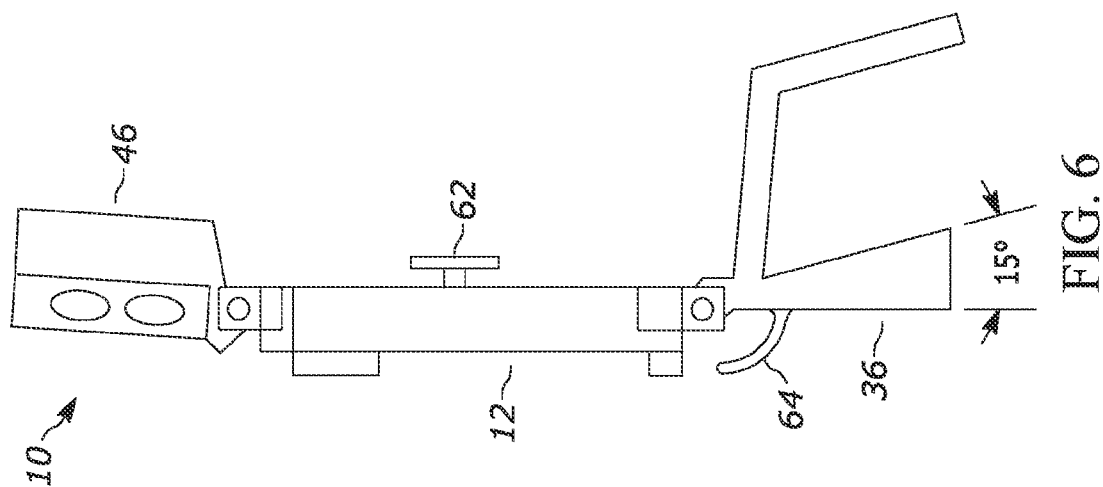
FIG. 6 is a side view of a medical device in a non-extended configuration according to an aspect of the present invention.
Figure 9:
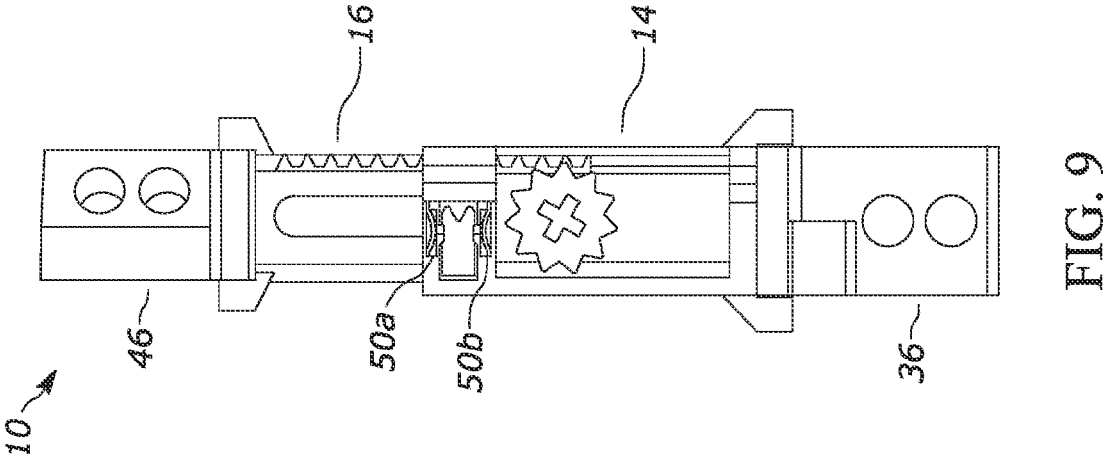
FIG. 9 is a top view of the medical device of FIG. 8.
Figure 8:
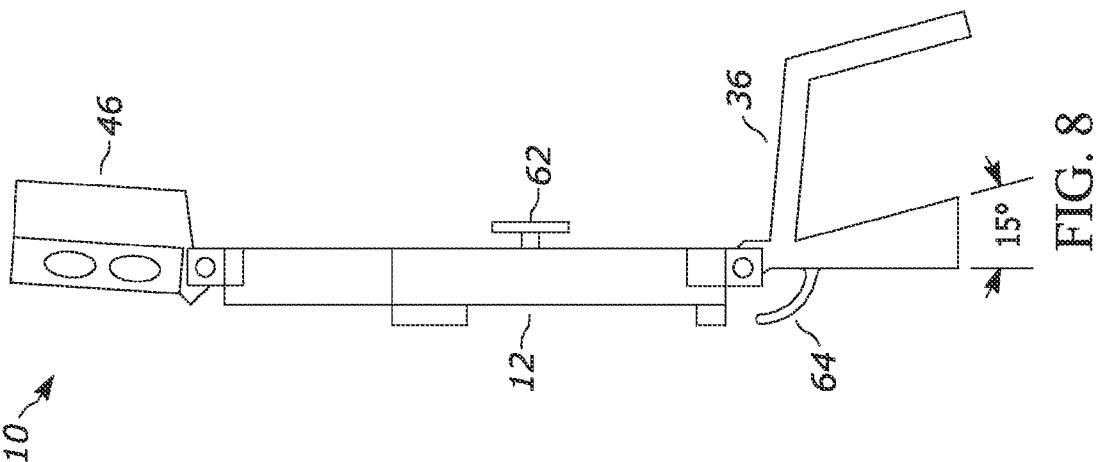
FIG. 8 is a side view of the medical device of FIG. 6 in an extended configuration according to an aspect of the present disclosure.
Figure 22:
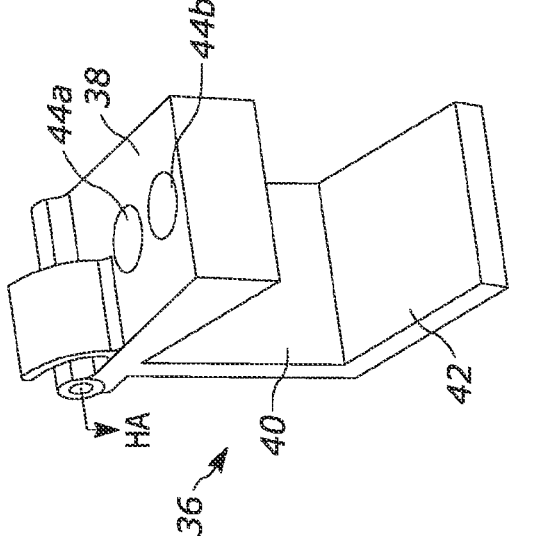
FIG. 22 is a perspective view of a laminar shelf portion of a medical device according to an aspect of the present disclosure.

Laminar shelf portion 36 can be hingedly connected to a second end of the main housing, such as second end portion 28 of outer housing 14 so that the laminar shelf portion can rotate about the outer housing. Referring to FIG. 22, laminar shelf portion 36 can have top face 38, side face 40 and bottom face 42 sized and configured to be disposed against a lamina of a patient (as described below). Bone screw holes 44a and 44b can extend through laminar shelf portion that can accept bone screws to attach the laminar shelf portion to the patient's lamina. Although only two bone screw holes are illustrated in the figures, the laminar shelf portion can include any number of suitable bone screw holes to fixate the laminar shelf portion to the lamina of a patient's vertebra (e). Referring to FIGS. 6 and 8, the top and bottom faces of the laminar shelf portion can be tilted by approximately 15 degrees to increase the screw drill length. On the laminar shaft side, the shelf can be tilted around the longitudinal axis of the implant to provide optimal screw length inside the bone.

Figure 25:
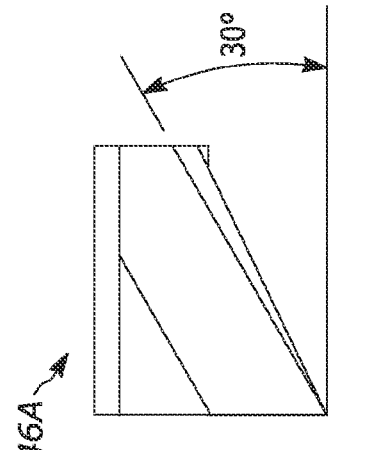
FIG. 25 is a side view of the lateral mass connection portion of FIG. 24.
Figure 24:
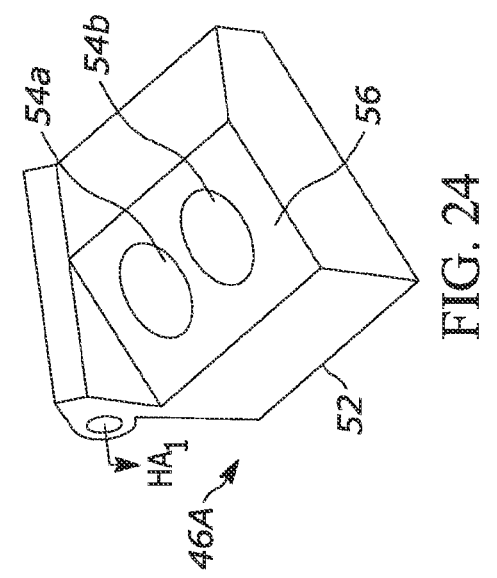
FIG. 24 is a perspective view of a lateral mass connection portion of a medical device according to an aspect of the present disclosure.
Figure 27:
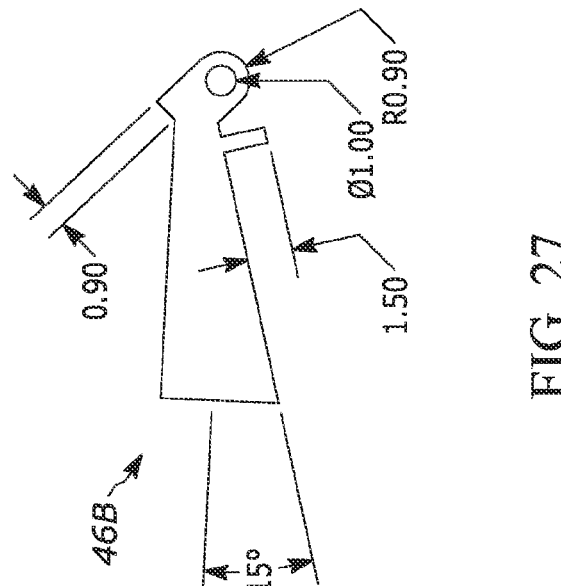
FIG. 27 is a side view of the lateral mass connection portion of FIG. 26.
Figure 26:
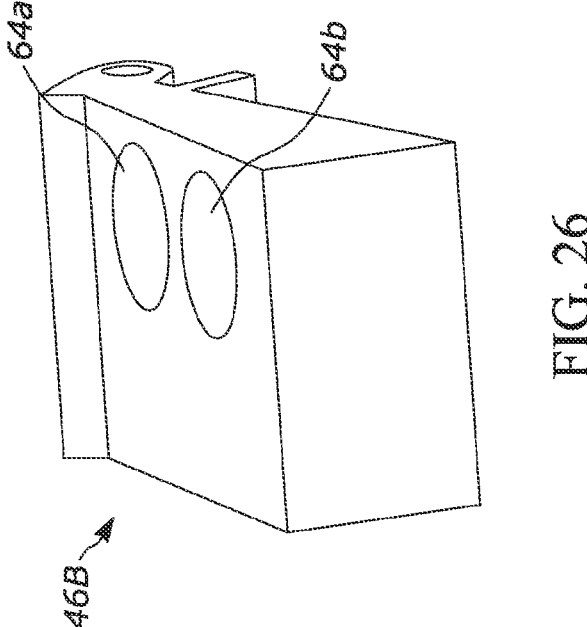
FIG. 26 is a perspective view of a lateral mass connection portion of a medical device according to an aspect of the present disclosure.

Lateral mass connection portion 46 can be hingedly connected to second end of the main housing such as second end 48 of inner housing 16 so that the lateral mass connection portion can rotate about the inner housing. Referring to FIG. 24, the lateral mass connection portion can have a top side 56 and a bottom side 52 and a bone screw hole 54 extending therethrough that can accept bone screws to attach the lateral mass connection portion to the patient's lateral mass. Although only two bone screw holes are illustrated in the figures, the lateral mass connection portion can include any number of suitable bone screw holes to fixate the lateral mass connection portion to the lateral mass of a patient's vertebra (e). Referring to FIGS. 24 and 25, the lateral mass connection portion can have an approximately 30-degree tilt with a rotation axis perpendicular to the hinge axis $HA_1$ of rotation to maximize screw length inside the superior articular facet. In this aspect, both the top side of the lateral mass connection portion and the screw holes are rotated approximately 30 degrees to provide sufficient contact between the implant and the bone. Referring to FIGS. 26 and 27, in certain aspects only the screw holes are rotated by 30 degrees to provide longer screw length.

Figures 4, 5:
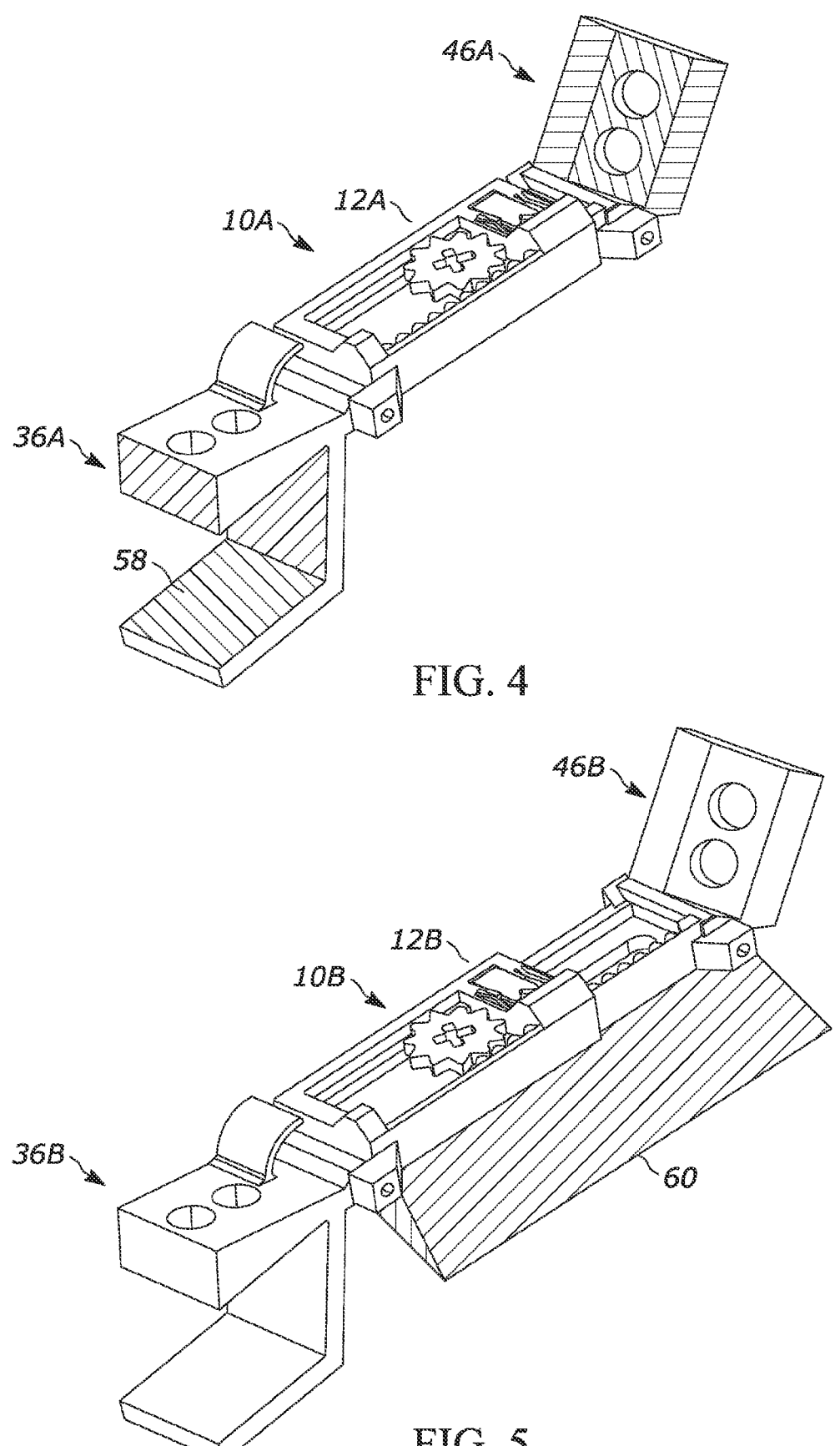
FIG. 4 is perspective view of a medical device in a non-extended configuration according to an aspect of the present disclosure.
FIG. 5 is a perspective view of a medical device in an extended configuration according to an aspect of the present disclosure.
Figure 7:
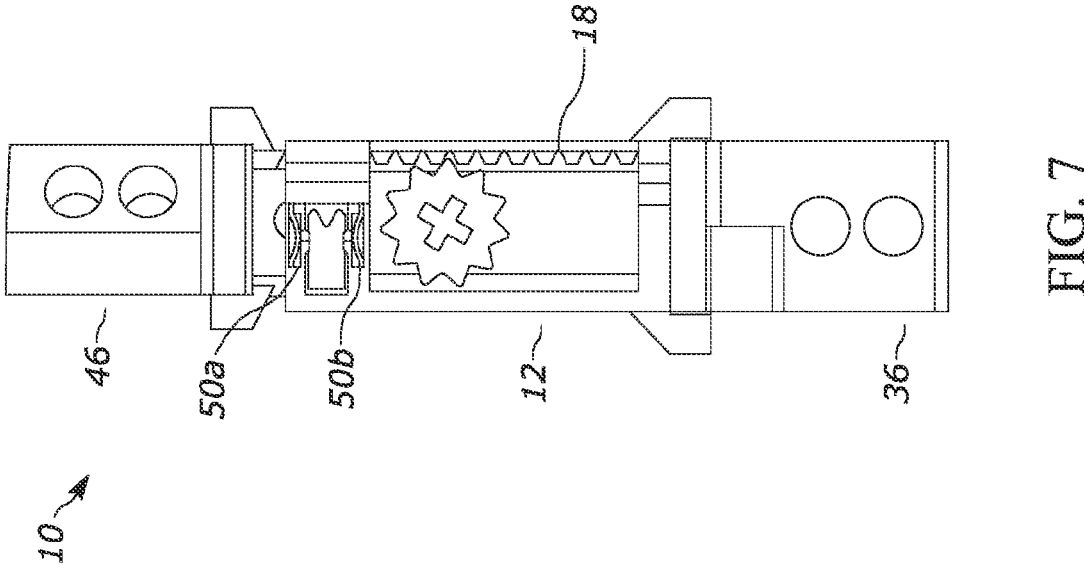
FIG. 7 is a top view of the medical device of FIG. 7

Referring to FIG. 4, implant 10A can have surface features 58 (depicted by hash lines) that can enhance cell attachment and/or bone ingrowth. Such features can be included on the surfaces touching bone (such as the lateral mass connection portion and the laminar shelf portion). Non-limiting surface features include surface roughening, additive features, inclusion of biological agents in addition to other surface features. Referring to FIG. 5, the implant can also include a bone graft (attached to the bottom of the main housing for example) to increase the union of bone to the implant.

Figure 10:
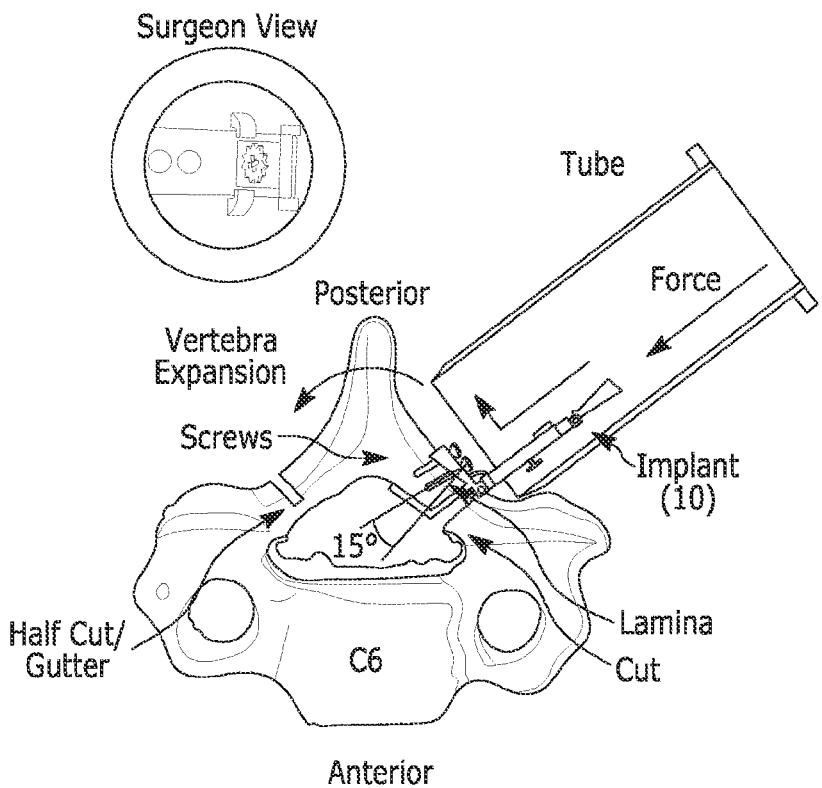
FIG. 10 is a schematic view depicting positioning of a medical device in a non-extended configuration according to an aspect of the present disclosure.
Figure 11:
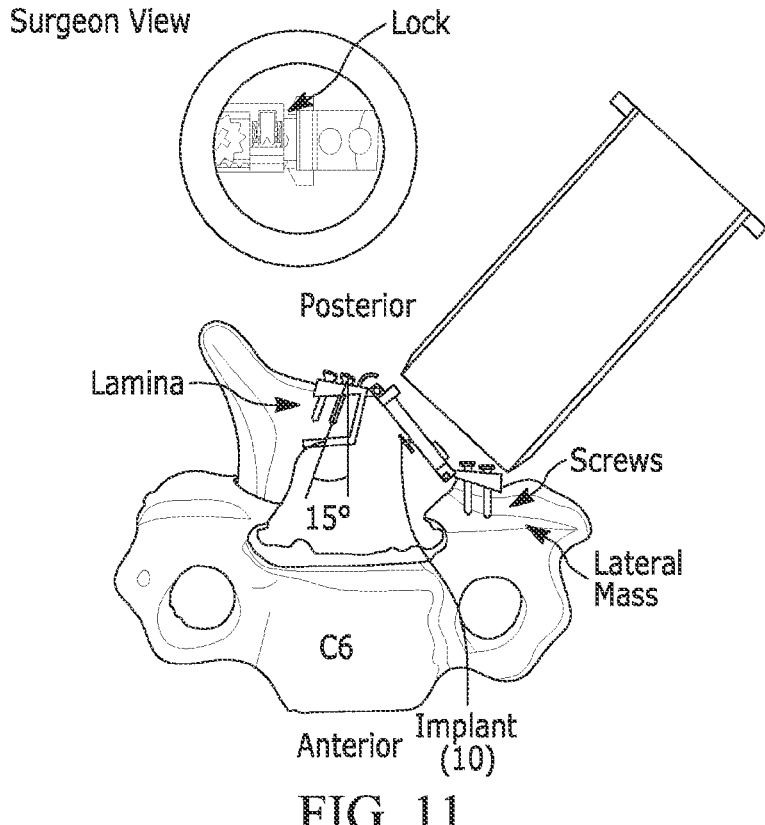
FIG. 11 is a schematic view depicting positioning of the medical device of FIG. 10 in an extended configuration.

FIGS. 10-11 illustrate an exemplary implantation of implant 10 using bone screws. The implant length can be continuously adjusted from a closed length of approximately 12.5 mm, to a fully open length of approximately 25 mm providing an adjustment range 3 times that of current implants (e.g. 4 mm). The expansion can be achieved via rotation of the gear, which allows a continuous and smooth expansion of the vertebral lamina as well as measurement of the expansion force using the torque applied to the gear. The control over the expansion force is beneficial because it can prevent the breakage of the vertebral bone at the gutter.

For open-door laminoplasty, before placing the implant, the vertebral lamina can be cut completely on one side, and partly on the other side, resulting in formation of a bony gutter, and creation of a hinge as shown in FIG. 10. Then the laminar shelf can be fixed to the lamina with bone screws. The shelf can be tilted approximately 15 degrees around the hinge axis of rotation to increase the screw length inside the lamina for better and stronger fixation. The free rotation around the hinge also provides a better and more natural connection to the lamina and avoids pre-stressing the connection. The implant can then be pushed downward to expand the vertebral lamina, and the lateral mass connection portion of the implant can be screwed to the lateral mass as shown in FIG. 11. In the case of an MIS surgery, at this step the gear and lock will be facing the MIS tube opening, allowing the surgeon to easily expand the vertebra by rotating the gear and then using the lock to fix the vertebral lamina in the open position. Similarly, double door laminoplasty can be performed using the implant via a MIS approach.

Figure 12:
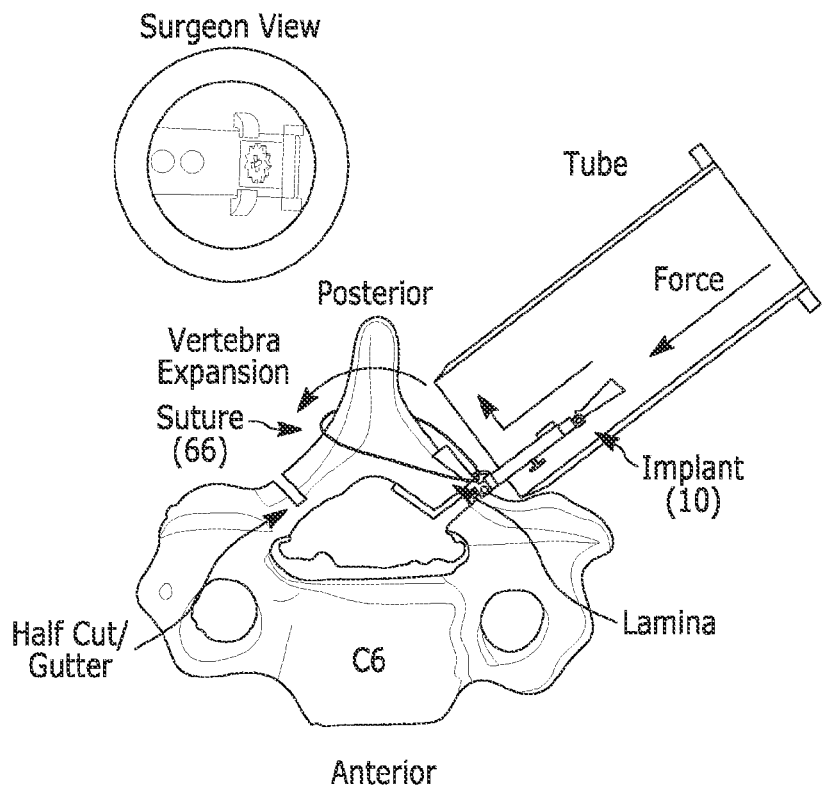
FIG. 12 is a schematic view depicting positioning of a medical device in a non-extended configuration according to an aspect of the present disclosure.
Figure 13:
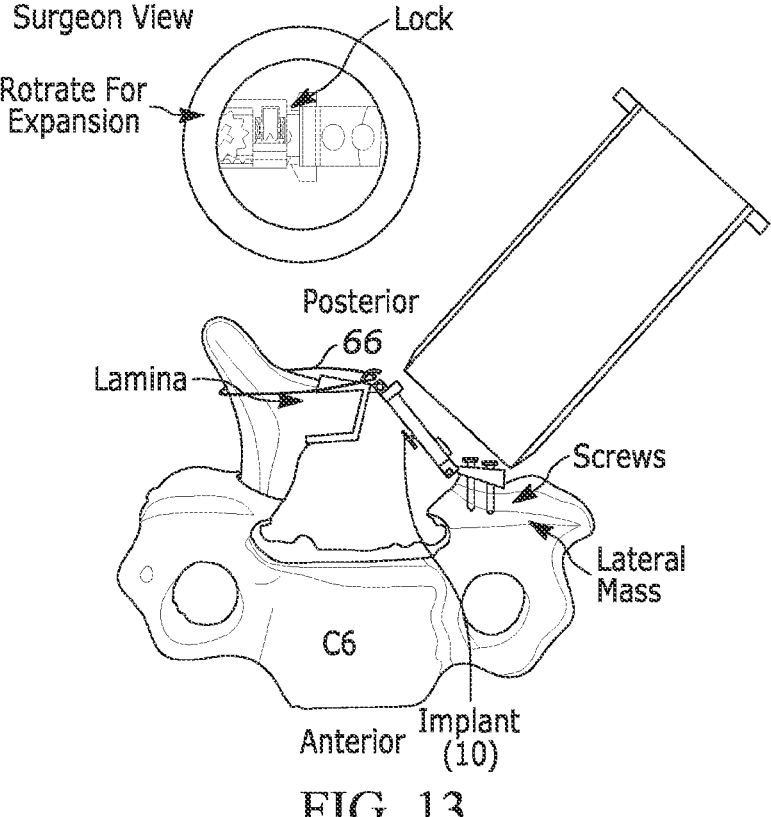
FIG. 13 is a schematic view depicting positioning of the medical device of FIG. 12 in an extended configuration.

Referring to FIGS. 12 and 13, the implant can also include a hook 64 illustrated in FIGS. 6 and 8 that is coupled to the laminar shelf portion, for example, to facilitate the usage of suture(s) 66 as an option instead of or in addition to screws, which can reduce possible screw misposition. The suture can be used instead of a screw for fixating the implant to the spinous process. One complexity for spine implants is the screw loosening due to the short penetration length of the screws in the vertebra. To address this issue, during implantation, there is a relative 15 degree angle between the lamina and the side portion of the laminar shelf portion shaft. This feature increases the screw penetration depth and transforms part of the shear stress at the threads into compressive stress hence helping with possible screw loosening.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Further, unless otherwise specified, none of the steps of the methods of the present disclosure are confined to any particular order of performance. Furthermore, all references cited herein are incorporated by reference in their entirety.

What is claimed is:

1. An implant comprising:
   a main housing comprising:
      an outer housing;
      an inner housing slidably receivable by the outer housing and comprising a gear rack;
   a gear disposed in the main housing and engageable with the gear rack of the inner housing to adjust the length of the main housing, the gear defining an aperture configured to accept a tool to translate rotational movement into linear motion, the inner housing having a first end receivable by a second end of the outer housing and slidably extendable through the outer housing until reaching an abutment wall at the second end of the outer housing to prevent further longitudinal movement of the inner housing;
   a lock slidably disposed in the main housing sized and configured to fix the length of the main housing when the desired length is achieved by slidable translation of the inner housing in the outer housing;
   a laminar shelf portion hingedly connected to a second end of the main housing, having a top portion, a side portion and a bottom portion sized and configured to be disposed against a lamina of a patient, the top portion defining bone screw holes extending therethrough; and
   a lateral mass connection portion hingedly connected to a first end of the main housing, having a top side and a bottom side and a bone screw hole extending therethrough, the bottom side sized and configured to be disposed against a lateral mass of a vertebrae of the patient.

2. The implant of claim 1, wherein the bone screw holes of the laminar shelf portion are angled approximately 15 degrees.

3. The implant of claim 1, wherein the lock is disposed in a chamber of the outer housing.

4. The implant of claim 3, further comprising springs located in the chamber that are sized and configured to engage the lock to maintain the lock in place and prevent the lock from backing out of the chamber.

5. The implant of claim 1, wherein the laminar shelf portion and the lateral mass connection portion include surface features to enhance cell attachment and bone ingrowth.

6. The implant of claim 1, wherein the implant further comprises a bone graft.

7. The implant of claim 1, wherein the laminar shelf portion is hingedly connected to the outer housing.

8. The implant of claim 1, wherein the lateral mass connection portion is hingedly connected to the inner housing.

9. The implant of claim 1, further comprising a hook extending from the laminar shelf portion or the main housing to receive a suture.

* * * * *